(12) United States Patent
Emaci et al.

(10) Patent No.: US 9,433,349 B2
(45) Date of Patent: Sep. 6, 2016

(54) SURFACE STATIONARY ARRAY COIL STRUCTURE FOR MULTI-MODALITY IMAGING

(71) Applicant: General Electric Company, Schenectady, NY (US)

(72) Inventors: Edward Emaci, Brookfield, WI (US); Michael James Calloway, Fort Atkinson, WI (US)

(73) Assignee: General Electric Company, Schenectady, NY (US)

( * ) Notice: Subject to any disclaimer, the term of this patent is extended or adjusted under 35 U.S.C. 154(b) by 315 days.

(21) Appl. No.: 13/943,884

(22) Filed: Jul. 17, 2013

(65) Prior Publication Data

US 2015/0025358 A1    Jan. 22, 2015

(51) Int. Cl.
| A61B 5/05 | (2006.01) |
| A61B 5/00 | (2006.01) |
| A61B 5/055 | (2006.01) |
| G01R 33/34 | (2006.01) |
| G01R 33/3415 | (2006.01) |
| G01R 33/48 | (2006.01) |

(52) U.S. Cl.
CPC ........... *A61B 5/0035* (2013.01); *A61B 5/0555* (2013.01); *G01R 33/34007* (2013.01); *G01R 33/3415* (2013.01); *G01R 33/481* (2013.01)

(58) Field of Classification Search
CPC .............. A61B 5/0035; A61B 5/0555; G01R 33/34007; G01R 33/3415; G01R 33/481
USPC ................................................. 600/407–430
See application file for complete search history.

(56) References Cited

U.S. PATENT DOCUMENTS

| 5,808,468 | A | 9/1998 | Bis et al. |
| 7,218,112 | B2 | 5/2007 | Ladebeck et al. |
| 7,923,691 | B2 | 4/2011 | Ladebeck |
| 2007/0003010 | A1* | 1/2007 | Guertin ................. G21K 1/093 378/63 |
| 2008/0015430 | A1 | 1/2008 | Takamori |
| 2008/0039712 | A1 | 2/2008 | Graves et al. |
| 2008/0088309 | A1 | 4/2008 | Eberler et al. |
| 2008/0312526 | A1 | 12/2008 | Gagnon et al. |

(Continued)

FOREIGN PATENT DOCUMENTS

| JP | 04020327 A | 1/1992 |
| JP | 06098873 A | 4/1994 |
| JP | 11113881 A | 4/1999 |

OTHER PUBLICATIONS

International Search Report and Written Opinion for PCT/US2014/046471, mail date Feb. 19, 2015, 23 pages.

*Primary Examiner* — Sanjay Cattungal (57) ABSTRACT

A stand-alone MR or hybrid PET-MR imaging system incorporating a surface stationary RF coil structure is disclosed. The imaging system includes a support assembly comprising a cradle to accommodate a subject and a bridge to receive the cradle and provide for translation therealong to enable an acquisition of imaging data. An RF coil structure is positioned between the bridge and the cradle, and includes a base portion, a cover portion, and an array of RF coil elements positioned on the cover portion. The cover portion includes contoured features that enable placement of RF coil elements in proximity to a subject and to provide a constant and uniform gap between the RF elements and the cradle. The RF coil structure also includes structural elements that support the cradle when rolling over the array of RF coil elements without deforming the RF coil elements.

13 Claims, 9 Drawing Sheets

(56) References Cited

U.S. PATENT DOCUMENTS

| | | |
|---|---|---|
| 2009/0209844 A1 | 8/2009 | Gagnon et al. |
| 2009/0299170 A1 | 12/2009 | Gebhardt et al. |
| 2010/0135559 A1 | 6/2010 | Morich et al. |
| 2010/0219347 A1 | 9/2010 | Schulz et al. |
| 2012/0059242 A1 | 3/2012 | Caruba et al. |
| 2013/0324835 A1 | 12/2013 | Menon et al. |

* cited by examiner

SURFACE STATIONARY ARRAY COIL STRUCTURE FOR MULTI-MODALITY IMAGING

BACKGROUND OF THE INVENTION

Embodiments of the invention relate generally to medical imaging, and more specifically, to a stand-alone magnetic resonance (MR) imaging system or hybrid MR and positron emission tomography (PET) system incorporating a surface stationary RF coil structure that provides patient support while reducing image degradation.

MR imaging involves the use of magnetic fields and excitation pulses to detect the free induction decay of nuclei having net spins. When a substance such as human tissue is subjected to a uniform magnetic field (polarizing field $B_0$), the individual magnetic moments of the spins in the tissue attempt to align with this polarizing field, but process about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

PET imaging involves the creation of tomographic images of positron emitting radionuclides in a subject of interest. A radionuclide-labeled agent is administered to a subject positioned within a detector ring. As the radionuclides decay, positively charged photons known as "positrons" are emitted therefrom. As these positrons travel through the tissues of the subject, they lose kinetic energy and ultimately collide with an electron, resulting in mutual annihilation. The positron annihilation results in a pair of oppositely-directed gamma rays being emitted at approximately 511 keV.

It is these gamma rays that are detected by the scintillators of the detector ring. When struck by a gamma ray, each scintillator illuminates, activating a photovoltaic component, such as a photodiode. The signals from the photovoltaics are processed as incidences of gamma rays. When two gamma rays strike oppositely positioned scintillators at approximately the same time, a coincidence is registered. Data sorting units process the coincidences to determine which are true coincidence events and sort out data representing deadtimes and single gamma ray detections. The coincidence events are binned and integrated to form frames of PET data which may be reconstructed into images depicting the distribution of the radionuclide-labeled agent and/or metabolites thereof in the subject.

In combination PET-MR systems, it is desirable to have minimum mass in the region of the PET detector in order to provide for optimum image acquisition. That is, while in a standalone MR system the structure and mass of components within the bore has no effect on image acquisition and image quality, such is not the case in a PET-MR system—as the mass in the PET detector region attenuates gamma rays, which reduces PET signal to the detectors and degrades image quality (IQ).

To minimize IQ attenuation, the design of both stationary and moving objects that are required to be in or go through the PET detector region should therefore be such so as to minimize mass in the PET detector region. Such stationary objects can include, for example, a patient positioning structure including a bridge positioned within the bore that extends through a length of the imaging system and a surface stationary radio frequency (RF) coil structure (e.g., posterior coil), while the moving object may comprise a cradle that supports the patient and translates along the bridge to move the patient through the imaging system.

With specific regard to the stationary posterior RF coil structure, the RF coil structure is positioned at the center of the MR and PET field of view (FOV) to acquire MR image data from the patient. The stationary posterior RF coil structure includes a number RF elements on its surface facing the bottom of the cradle that are in close proximity to the patient anatomy during an MR imaging scan, with a small gap being present between the RF coils and the cradle that keeps the cradle from rubbing on the coil elements as the cradle moves in and out of the magnet bore. Typically, any electronics associated with the stationary posterior RF coil structure, such as decoupling boards, feedboards, mux boards, and baluns for example, are positioned immediately adjacent the RF coil elements, and are thus also positioned at the center of the MR and PET FOV, thereby adding mass and additional components in the region of the PET detector and potentially reducing image quality.

Apart from PET image attenuation considerations, it is also recognized that the structure of the stationary posterior RF coil structure can affect MR image quality in a stand-alone MR imaging system or hybrid PET-MR system. That is, it is desirable to enable placement of the RF coil elements of the coil structure in close proximity with the patient anatomy so as to enable good MR image quality. In so positioning the RF coil elements, it is also desirable to provide a constant and uniform gap between the entire set of RF elements in the coil structure and a patient cradle surface. Existing designs of the stationary posterior RF coil structure provide a flat configuration or construction that lacks the curvature that is normally found on the patient cradle, such that existing posterior coil structure designs fail to position the RF coil elements in close proximity to the patient anatomy or provide such a uniform gap between the coil elements and the patient surface on the cradle.

It would therefore be desirable to provide a stationary posterior RF coil structure for use in a PET-MR system that helps in reducing the degradation of image quality by minimizing mass in the PET detector FOV. It would also be desirable for the stationary posterior RF coil structure to provide improved image quality without compromising on patient support functionalities and serviceability. It would still further be desirable to for the stationary posterior RF coil structure to include features thereon that enable placement of the RF coil elements for good proximity with patient anatomy, with such features following the contour of the cradle sides and enabling the coil elements to more closely view the patient anatomy where the sides of the patient move away from the horizontal cradle surface.

BRIEF DESCRIPTION OF THE INVENTION

Embodiments of the invention provide a stand-alone MR system or combined PET-MR system incorporating a stationary posterior RF coil structure that provides patient support for moving over the PET region while reducing image degradation and improving MR image quality on the sides of the patient with wing-like structures with RF elements that follow the cradle contour.

In accordance with one aspect of the invention, a PET-MRI apparatus includes a magnetic resonance imaging (MRI) system having a plurality of gradient coils positioned about a bore of a magnet, and an RF coil assembly coupled to a pulse generator to emit an RF pulse sequence and arranged to receive resulting MR signals from a subject of interest in the bore within an MR field-of-view (FOV). The PET-MRI apparatus also includes a positron emission tomography (PET) system having a detector array encircling the bore, with the detector array being controlled to acquire PET emissions of the subject of interest within a PET detector FOV, and a patient support assembly configured to provide for support and movement of the subject of interest through the bore to enable acquisition of the MR signals and the PET emissions from the subject of interest, the patient support assembly comprising a cradle configured to accommodate the subject of interest and a bridge configured to receive the cradle and provide for translation therealong. The PET-MRI apparatus further includes a stationary radio frequency (RF) coil structure positioned on the bridge so as to be between the bridge and the cradle and such that a portion of the RF coil structure is within the PET FOV, the RF coil structure comprising a base portion, a cover portion positioned over the base portion, an array of RF coil elements positioned on the cover portion so as to be positioned within the MR FOV and PET FOV, and driver electronics configured to control operation of the array of RF coil elements, the driver electronics being positioned within the base portion so as to be positioned outside of the PET FOV.

In accordance with another aspect of the invention, a stationary posterior RF coil structure for use in a stand-alone MR imaging system or a combination PET-MR imaging system includes a base portion, a cover portion positioned over the base portion, an array of RF coil elements positioned on the cover portion and, in a first region of the RF coil structure, and driver electronics configured to control operation of the array of RF coil elements, the driver electronics being positioned in the base portion, in a second region of the RF coil structure, so as to be separated from the array of RF coil elements. The cover portion further includes a bottom surface and a pair of contoured side surfaces extending up from the bottom surface, wherein the array of RF coil elements is arranged and positioned on the cover portion so as to extend from the bottom surface up the pair of contoured side surfaces.

In accordance with yet another aspect of the invention, an MR imaging apparatus includes an MRI system configured to acquire MR signals from a subject of interest, the MRI system having a plurality of gradient coils positioned about a bore of a magnet and an RF coil assembly coupled to a pulse generator to emit an RF pulse sequence. The MR imaging apparatus also includes a patient support assembly configured to provide for support and movement of the subject of interest through the bore to enable acquisition of the MR signals from the subject of interest, the patient support assembly comprising a cradle configured to accommodate the subject of interest and a bridge configured to receive the cradle and provide for translation therealong. The MR imaging apparatus further includes a central matrix array (CMA) structure positioned on the bridge so as to be between the bridge and the cradle, the CMA structure comprising a base portion, a cover portion attached to the base portion so as to be positioned between the base portion and the cradle, an array of RF coil elements positioned on the cover portion, and a plurality of structural members extending upward from a bottom surface of the base portion, the plurality of structural members being configured to fully support a load applied by the cradle as the cradle translates the subject of interest through the bore, without any of the load being transferred to the array of RF coil elements.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

A stationary posterior RF coil structure for use in a stand-alone MR imaging system or hybrid PET-MR system is provided. The RF coil structure is constructed so as to arrange RF coil elements thereon so as to provide a constant and uniform gap between the entire set of RF elements and a patient cradle surface so as to enable good MR image quality. The RF coil structure is further constructed to include structural elements that enable the cradle to roll over the posterior stationary RF coil, as the cradle moves thru the magnet bore, without deforming the RF coil elements—so as to enable stable image quality with any patient mass. The stationary posterior RF coil structure is still further constructed to have a minimal mass in the PET detector region (i.e., PET gap) by providing minimal electrical and mechanical components in the PET gap and moving all large mass components away from the PET gap, so as to enable good PET image quality.

According to embodiments of the invention, the stationary posterior RF coil structure can be implemented in a variety of imaging systems or apparatuses. For example, the RF coil structure can be incorporated into a stand-alone MR imaging system or can be incorporated into a hybrid MR imaging system, such as a hybrid PET-MR imaging system, for example. Thus, while embodiments of the invention are set forth here below with respect to a hybrid PET-MR imaging system, it is recognized that other stand-alone and hybrid MR imaging systems are considered to be within the scope of the invention.

Figure 1:
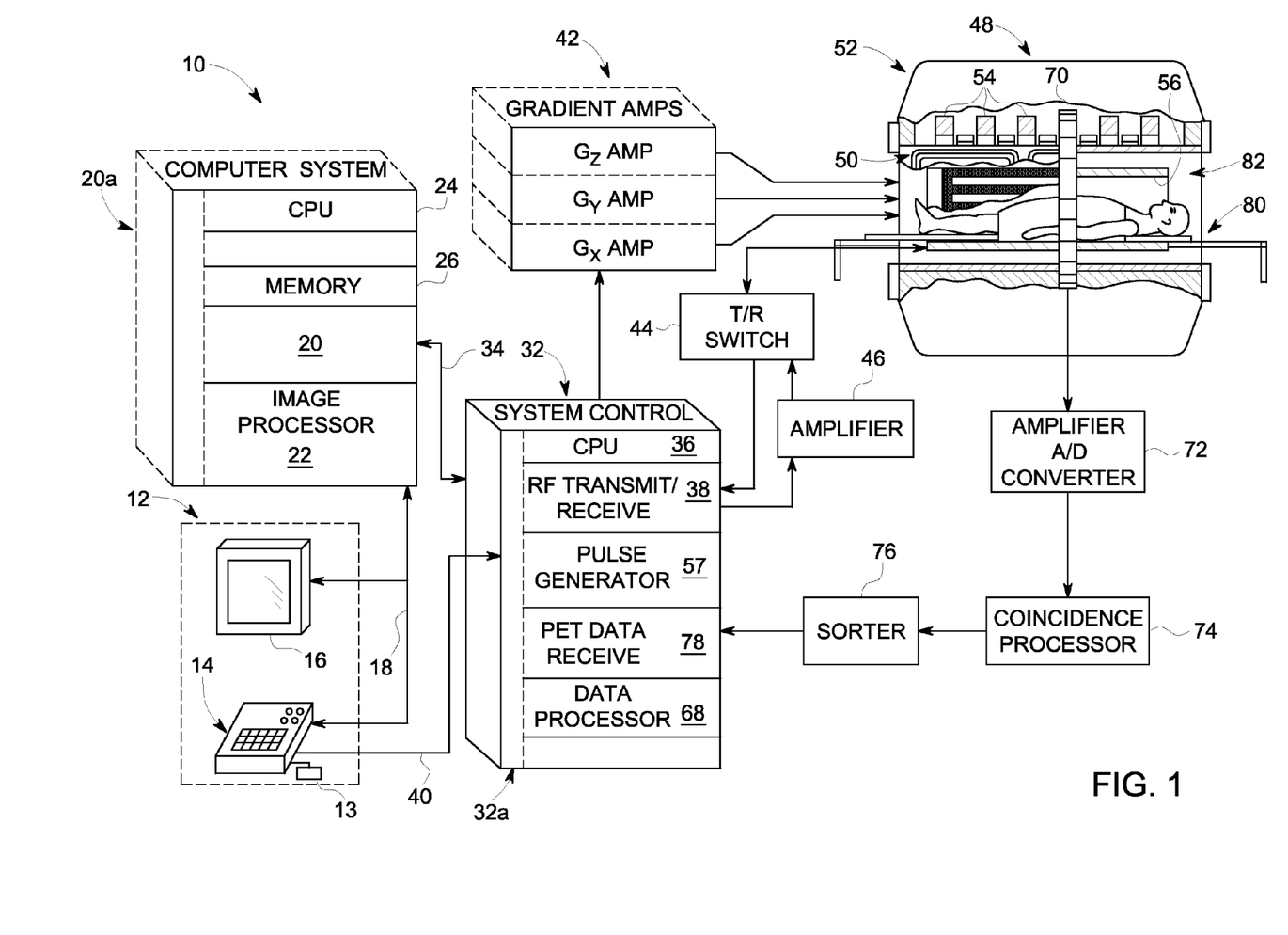
FIG. 1 is a schematic block diagram of an exemplary PET-MR imaging system for use with an embodiment of the invention.

Referring to FIG. 1, the major components of an exemplary hybrid PET-MR imaging system 10 that may incorporate embodiments of the present invention are shown. The operation of the system may be controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules, such as an image processor module 22, a CPU module 24 and a memory module 26. The computer system 20 may also be connected to permanent or back-up memory storage, a network, or may communicate with a separate system control 32 through link 34. The input device 13 can include a mouse, keyboard, track ball, touch activated screen, light wand, or any similar or equivalent input device, and may be used for interactive geometry prescription.

The system control 32 includes a set of modules in communication with one another and connected to the operator console 12 through link 40. It is through link 34 that the system control 32 receives commands to indicate the scan sequence or sequences that are to be performed. For MR data acquisition, an RF transmit/receive module 38 commands the scanner 48 to carry out the desired scan sequence, by sending instructions, commands, and/or requests describing the timing, strength and shape of the RF pulses and pulse sequences to be produced, to correspond to the timing and length of the data acquisition window. In this regard, a transmit/receive switch 44 controls the flow of data via amplifier 46 to scanner 48 from RF transmit module 38 and from scanner 48 to RF receive module 38. The system control 32 also connects to a set of gradient amplifiers 42, to indicate the timing and shape of the gradient pulses that are produced during the scan.

The gradient waveform instructions produced by system control 32 are sent to the gradient amplifier system 42 having Gx, Gy, and Gz amplifiers. Amplifiers 42 may be external of scanner 48 or system control 32, or may be integrated therein. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and an RF coil assembly 56. Alternatively, the gradient coils of gradient coil assembly 50 may be independent of the magnet assembly 52. RF coil assembly may include a whole-body RF transmit coil 56 as shown. The coils 56 of the RF coil assembly may be configured for both transmitting and receiving, or for transmit-only or receive-only. A pulse generator 57 may be integrated into system control 32 as shown, or may be integrated into scanner equipment 48, to produce pulse sequences or pulse sequence signals for the gradient amplifiers 42 and/or the RF coil assembly 56. In addition, pulse generator 57 may generate PET data blanking signals synchronously with the production of the pulse sequences. These blanking signals may be generated on separate logic lines for subsequent data processing. The MR signals resulting from the excitation pulses, emitted by the excited nuclei in the patient, may be sensed by the whole body coil 56 and are then transmitted to the RF transmit/receive module 38 via T/R switch 44. The MR signals are demodulated, filtered, and digitized in the data processing section 68 of the system control 32.

An MR scan is complete when one or more sets of raw k-space data has been acquired in the data processor 68. This raw k-space data is reconstructed in data processor 68 which operates to transform the data (through Fourier or other techniques) into image data. This image data is conveyed through link 34 to the computer system 20 where it is stored in memory 26. Alternatively, in some systems computer system 20 may assume the image data reconstruction and other functions of data processor 68. In response to commands received from the operator console 12, the image data stored in memory 26 may be archived in long term storage or may be further processed by the image processor 22 or CPU 24 and conveyed to the operator console 12 and presented on the display 16.

In combined MR-PET scanning systems, PET data may be acquired simultaneously with the MR data acquisition described above. Thus, scanner 48 also contains a positron emission detector array or ring 70, configured to detect gamma rays from positron annihilations emitted from a subject. Detector array 70 preferably includes a plurality of scintillators and photovoltaics arranged about a gantry. Detector array 70 may, however, be of any suitable construction for acquiring PET data. In addition, the scintillator packs, photovoltaics, and other electronics of the detector array 70 need not be shielded from the magnetic fields and/or RF fields applied by the MR components 54, 56. However, it is contemplated that embodiments of the present invention may include such shielding as known in the art, or may be combined with various other shielding techniques.

Gamma ray incidences detected by detector array 70 are transformed, by the photovoltaics of the detector array 70, into electrical signals and are conditioned by a series of front-end electronics 72. These conditioning circuits 72 may include various amplifiers, filters, and analog-to-digital converters. The digital signals output by front end electronics 72 are then processed by a coincidence processor 74 to match gamma ray detections as potential coincidence events. When two gamma rays strike detectors approximately opposite one another, it is possible, absent the interactions of random noise and signal gamma ray detections, that a positron annihilation took place somewhere along the line between the detectors. Thus, the coincidences determined by coincidence processor 74 are sorted into true coincidence events and are ultimately integrated by data sorter 76. The coincidence event data, or PET data, from sorter 76 is received by the system control 32 at a PET data receive port 78 and stored in memory 26 for subsequent processing 68. PET images may then be reconstructed by image processor 22 and may be combined with MR images to produce hybrid structural and metabolic or functional images. Conditioning circuits 72, coincidence processor 74 and sorter 76 may each be external of scanner 48 or system control 32, or may be integrated therein.

As further shown in FIG. 1, a patient support assembly 80 is included in PET-MR imaging system 10 to support the patient within the imaging system during data acquisition. The patient support assembly 80 extends into a main magnet bore 82 of the imaging system 10 and extends through the imaging system so that its length is generally parallel to the bore axis. The patient support assembly 80 enables movement of the patient into various positions with respect to the imaging system 10, including a loading position outside the bore of imaging system 10 and at least one imaging position, where at least a portion of a patient is positioned within an imaging volume (i.e., within the bore) when at the imaging position.

Figure 2:
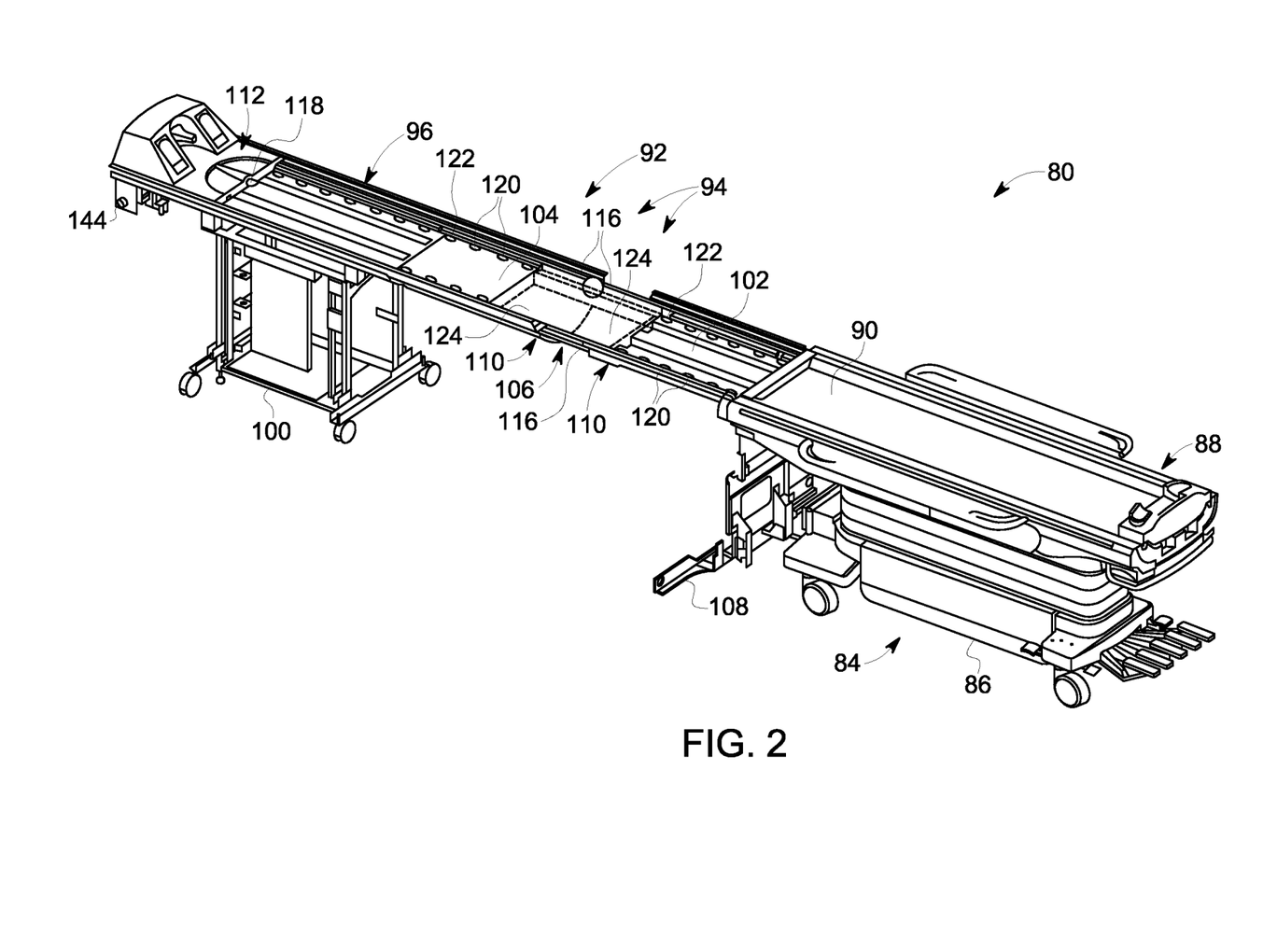
FIG. 2 is a perspective view of a patient support assembly for use in the PET-MR imaging system of FIG. 1 according to an embodiment of the invention.
Figure 3:
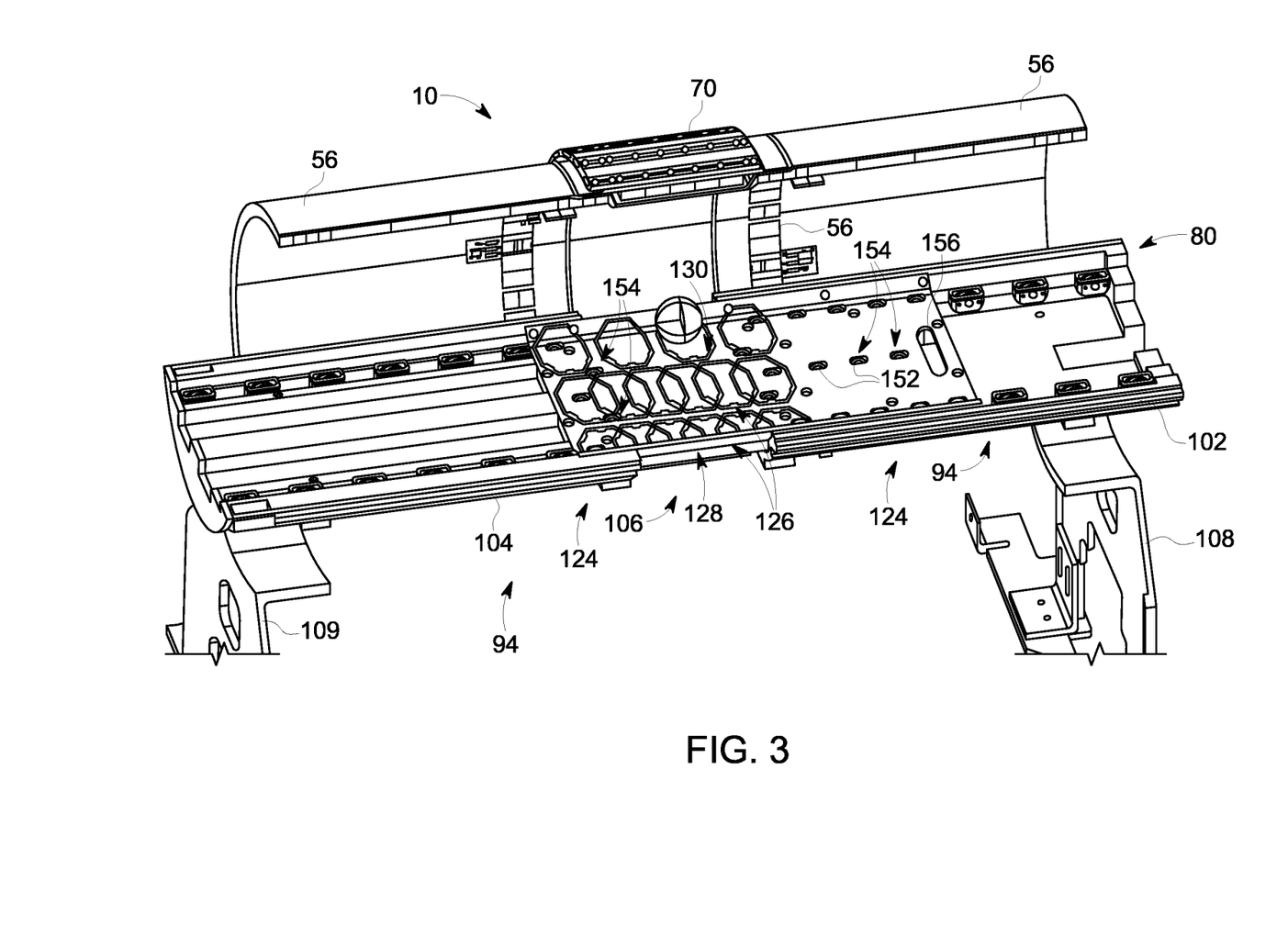
FIG. 3 is a view of a stationary posterior RF coil structure positioned relative to the patient support assembly of FIG. 2 according to an embodiment of the invention.

Referring now to FIGS. 2 and 3, detailed views of patient support assembly 80 are shown according to an embodiment of the invention. The patient support assembly 80 includes a patient bed 84 that supports the patient and provides for transport of the patient to and from the imaging system 10. The patient bed 84 includes a base structure 86 and a table 88 that is removable from the base structure 86 to enable transfer of the patient from the bed into the bore 82 of the PET-MR imaging system 10 for performing of an imaging scan. The table 88 further includes a cradle 90 that facilitates movement of the table through the imaging system 10. The surface of cradle 90 has straight and curved surfaces—with the main surface that the patient lays on being flat and the sides of the cradle curving in an angular manner to provide comfort and maximize patient space. According to an exemplary embodiment, the cradle 90 is constructed as a thin, Kevlar cradle. The height of the patient bed 84 may be adjusted as needed in order to position the table 88 appropriately for transfer of the patient into the imaging system 10, such that the cradle 90 may slide off of the base structure 86 and into the imaging system 10.

Also included in patient support assembly 80 is a bridge assembly 92 having a front bridge 94, comprised of two separate sections (patient side and service side), and a rear bridge 96. The bridge assembly 92 provides a path for the patient cradle 90 to move within and through the bore 82 of imaging system 10 (FIG. 1) to move the patient to desired imaging locations within the imaging system. According to an exemplary embodiment, the rear bridge 96 and front bridge 94 have a construction of a foam core with a skin of Kevlar or another fiber reinforced plastic (FRP), so as to provide a strong bridge with structure capable of holding a large patient with minimal deformation while minimizing weight for field service removal and installation.

As seen in FIG. 2, the rear bridge 96 extends outward from a rear edge of imaging system 10, with the rear bridge 96 being supported by a rear pedestal structure 100. The front bridge 94 has a split bridge configuration and includes a first section 102 (patient side) and a second section 104 (service side) that are separated from one another by a gap 106. The first section 102 and the second section 104 are supported by, and mounted to the RF body coil 56 at multiple locations. The RF body coil 56 is mounted to front and rear body coil mounting brackets 108 and 109, with the both brackets 108 and 109 providing adjustability regarding connection of the body coil 56 relative to the magnet 54. Front bridge patient-side 102 and front bridge service-side 104 can be made to be adjustable or non-adjustable during mounting to RF body coil 56. An outer edge of second section 104 is assembled with and connected to rear pedestal structure 100 so as to be supported in the axial direction thereby. An inner edge 110 of each of the first and second sections 102, 104 is mounted directly to the imaging system 10 (i.e., to RF body coil 56 of the imaging system) so as to be anchored thereto.

The inner edge 110 of each of the first and second sections 102, 104 of front bridge 94 is located adjacent to either side of detector array 70 of imaging system 10 (FIG. 1), such that the detector array 70 is aligned with the gap 106 between the first and second sections 102, 104. Beneficially, the aligning of the detector array 70 and the gap 106 between the first and second sections 102, 104 of front bridge 94 minimizes mass in the region of the detector array 70, so as to thereby reduce the attenuation of gamma rays during PET imaging that may result from the presence of such mass. The PET signal received by the detectors in detector array 70 is thus not attenuated and the degradation of the image quality (IQ) is minimized.

A low profile carriage assembly (LPCA) 112 is also included in patient support assembly 80 for purposes of enabling the translation of cradle 90 along bridge assembly 92. The LPCA 112 is driven by a dual belt drive 144 that includes a pair of drive belts 116 for propelling the LPCA 112 along a length of the bridge assembly 92, (and over a posterior coil array in the bridge—as will be explained in more detail below), with the belts extending over gap 106, such that LPCA 112 and cradle 90 continue to be driven by dual drive even when traversing the gap 106. As shown in FIG. 2, the LPCA 112 may originally be positioned at a far end of rear bridge 96. When a patient is transported to PET-MR imaging system 10 via patient bed 84 for purposes of an imaging scan, the LPCA 112 is driven by dual belt drive 144 along rear bridge 96 and along front bridge 94 (and over a posterior coil array in the front bridge—as will be explained in more detail below), to be brought into proximity of patient bed 84. The LPCA 112 is brought into contact with cradle 90 of the patient table 88, such that a hook 118 or similar type latching mechanism is caused to engage a receptacle or receiving mechanism (not shown) on cradle 90. Upon securing of LPCA 112 to cradle 90, the LPCA 112 and cradle 90 may be translated along bridge assembly 92 as desired to position the patient in a plurality of imaging positions within bore 82 of imaging system 10.

As shown in FIG. 2, the rear bridge 96 and the front bridge 94 each include a plurality of vertically oriented roller bearings or wheels 120 spaced along a length of the front and rear bridges 94, 96 for supporting cradle 90 and LPCA 112 during translation thereof along the entire scan range, with pairs of spaced apart roller bearings 120 being positioned along a length of the front and rear bridges 94, 96. A number of horizontally oriented tapered wheels 122 (or similar guiding devices) is also included on rear bridge 96 and the front bridge 94 at select locations. The horizontally oriented tapered wheels 122 function to assist in laterally positioning cradle 90 and LPCA 112 on bridge assembly 92, such that the cradle 90 and LPCA 112 remain centered on the bridge assembly 92.

Referring still to FIG. 2, it is seen that each of the first and second sections 102, 104 of front bridge 94 includes a cut-out area or portion 124 therein in an area adjacent the inner edge 110 of the respective first and second sections 102, 104, next to gap 106. The cut-out areas 124 of the first and second sections 102, 104 of front bridge 94 collectively form an area for housing an array of radio frequency (RF) coils that form part of a stationary posterior RF coil structure of the PET-MR imaging system 10. Such a stationary posterior RF coil structure 126, or central matrix array (CMA) structure, is shown positioned relative to patient support assembly 80 in FIG. 3, with the CMA structure 126 being positioned at least partially within cut-out areas 124 of the first and second sections 102, 104 of front bridge 94.

More detailed views of the CMA structure 126 are provided in FIGS. 4-7, where various views of the CMA structure are shown. As can be seen in FIGS. 4-8, CMA structure 126 generally includes a base portion 128 and a cover portion 130. The base portion 128 of the CMA structure is configured as a box-like structure that is positionable in cut-out areas 124 (FIGS. 2-3), with the cover portion 130 being applied over the base portion 128 so as to be positioned between the base portion 128 and cradle 90 of the patient support assembly 80.

Figure 4:
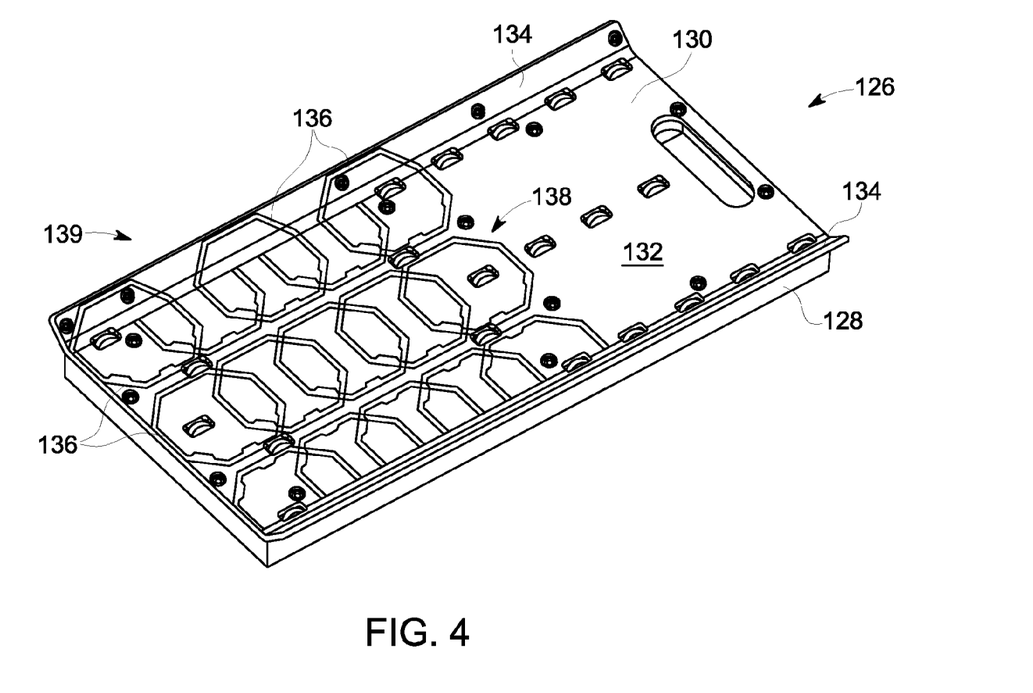
FIGS. 4-7 are views of the stationary posterior RF coil structure of FIG. 3 according to an embodiment of the invention.
Figure 5:
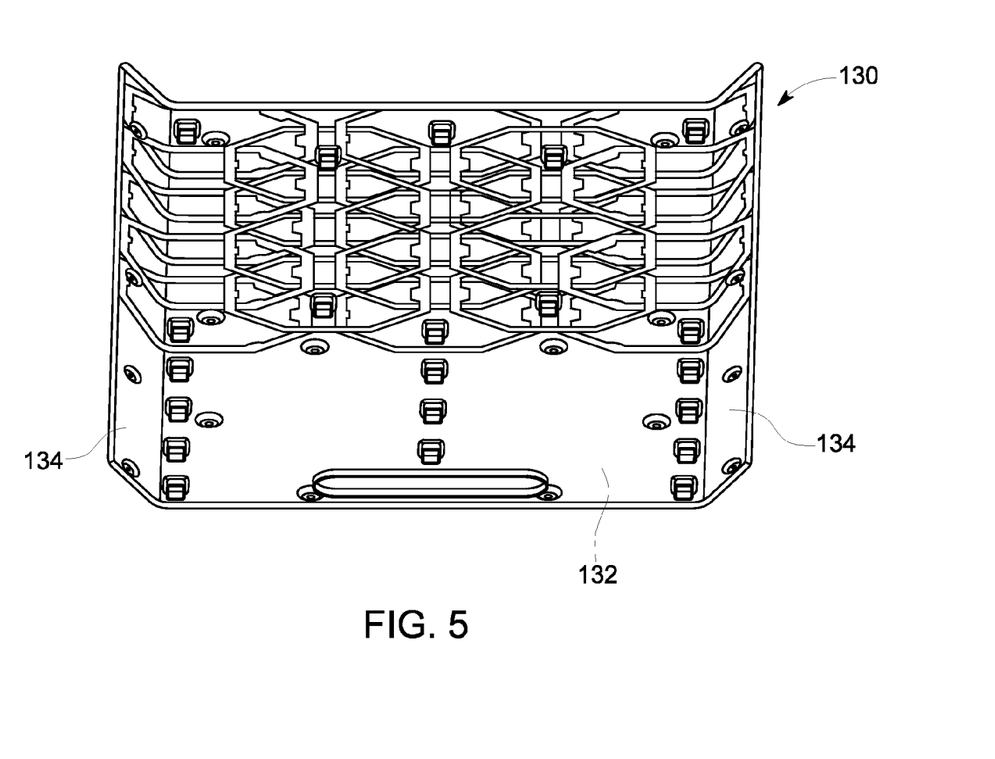
Figure 6:
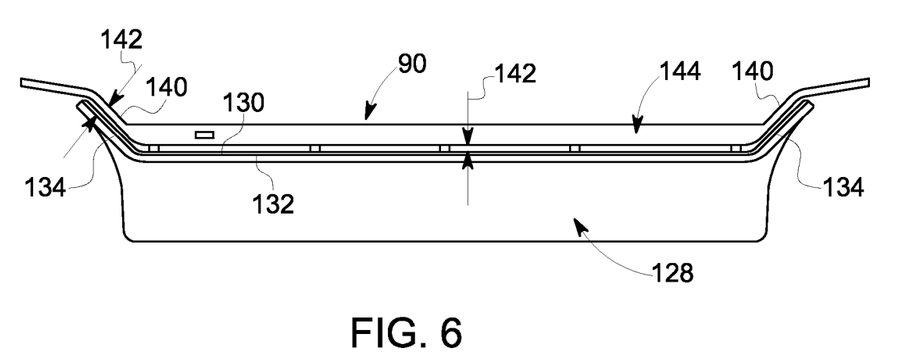

Referring to FIGS. 4-6, an embodiment of the cover portion 130 is shown according to an exemplary embodiment. The cover portion 130 includes a flat surface 132 in a central region thereof and a pair of angled/contoured side surfaces or "wings" 134 that are positioned on opposing sides of the bottom surface 132. The cover portion 130 receives a plurality of RF coil elements 136 therein that collectively form an RF coil array or central matrix array (CMA), generally indicated as 138. The RF coil elements 136 are positioned on the cover portion 130 such that the coil elements face the bottom of the cradle 90 and are positioned in close proximity to the patient anatomy during an MRI scan, with the RF coil array 138 being positioned on cover portion 130 such that the RF coil array 138 is aligned with the PET detector array 70 of PET-MR system 10 (FIGS. 1 and 3)—in what is termed generally as a "first region" 139 of the coil structure 126.

As further shown in FIGS. 4 and 5, the coil elements 136 of RF coil array 138 extend out from the flat surface of cover portion 130 and out onto angled/contoured side surfaces 134 of the cover 130 so as to extend at least a portion of the way there up. The RF coil elements 136 positioned on angled/contoured surfaces 134 thus are angled and point toward the body of the patient. As can best be seen in FIG. 6, the angle and positioning of angled/contoured side surfaces 134 of cover portion 130 generally matches that of curved side surfaces 140 of cradle body 90. Therefore, a constant and uniform gap 142 is provided between the entire RF coil array 138 and the cradle 90, both between the RF coil elements 136 on the flat center area 132 of the cover portion 130 and the flat surface 144 of cradle 90 and between the RF coil elements 136 on the angled/contoured side surfaces 134 of the cover portion 130 and the curved side surfaces 140 of cradle 90. This uniform and minimal gap 142 between the RF coil array 138 and patient surface on the cradle 90 produces good MR image quality.

Figure 7:
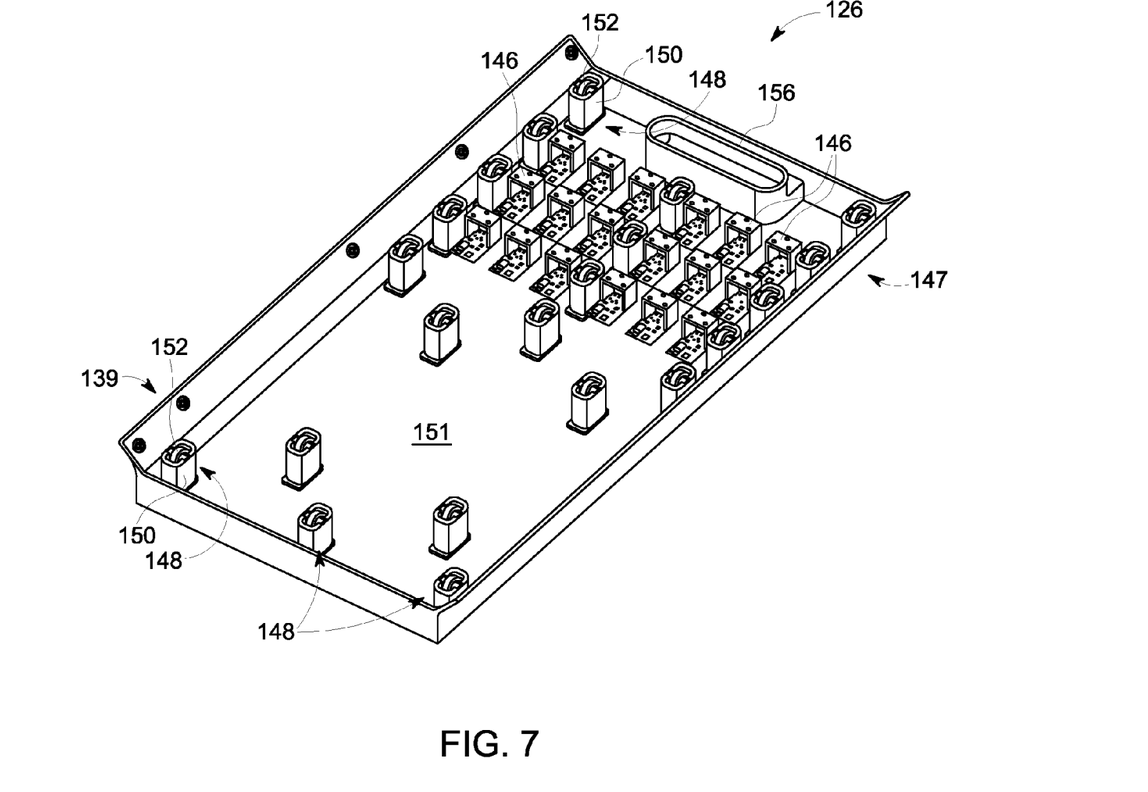

Referring now to FIG. 7, in order to minimize the mass of material/components positioned within a FOV of the PET detector array 70 (FIGS. 1 and 3), remote electronics 146 associated with operation of the RF coil array, including decoupling boards, feedboards, mux boards, baluns, and other non-essential components, for example, are positioned in the base portion 128 so as to be distanced from the RF coil array 136 on the cover portion 130 (FIGS. 4 and 5)—in what is termed generally as a "second region" 147 of the coil structure 126. The remote electronics 146 are thus moved away from the PET detector region so as to minimize the mass of material of the CMA structure 126 at its center region in the S/I and R/L directions in the PET field of view.

As further shown in FIG. 7, base portion 128 also includes a plurality of structural elements 148 therein that enable the cradle 90 and LPCA 112 to roll over the CMA structure 126, by fully supporting a patient mass with ancillary MR and PET items. The structural elements 148 in the CMA structure 126 provide needed support for a split front bridge 94 that has no structure in the PET imaging region, with structural elements 148 closest to the PET gap enabling the cradle 90 to span the gap 106 without significant cantilever-type deformation. The structural elements 148 of the base portion 128 are comprised of vertical mounting columns 150 that are formed integrally with a bottom surface 151 of base portion 128, with the mounting columns 150 extending upwardly from the bottom surface 151. A vertically oriented rolling element or bearing 152 is positioned on top of each respective mounting column 150 at a height that enables the rolling element 152 to engage a bottom surface of cradle 90.

As can be seen in FIG. 7, a majority of structural members 148 are located outside of the first region 139 of CMA structure 126 (i.e., in the second region 147), so as to further minimize the mass of material of the CMA structure 126 at it's center region in the S/I and R/L directions in the PET field of view. Regarding the location of structural members 148, while a majority thereof are located outside of the first region 139 of CMA structure 126, the structural members 148 are still positioned so as to fully support the cradle 90 and the patient mass thereon so as to prevent any load from being transferred to the RF coil array 138. That is, the structural members 148 (and rolling elements 152 thereon) of the CMA structure 126 are placed in strategic locations and quantities as to not interfere with the RF coil element 136 configuration and to provide good surface contact stress between the rolling elements 152 and the cradle 90.

In order to provide for accommodation of the cradle 90 as it traverse across gap 106 of patient support assembly 80 and as it traverses across the location where CMA structure 126 is positioned, the cover portion 130 of the CMA structure includes a plurality of openings/slots 154 formed therein at locations corresponding to the locations of structural members 148 formed on the base portion 128, as can be seen in FIGS. 4 and 5. The openings 154 are configured and positioned such that roller bearings 152 on the structural members 148 pass through the open slots on the cover portion 130, such that the roller elements 152 come in contact with a bottom surface of cradle 90 and provide for structural support and a rolling translation of the cradle 90 across the CMA structure 126 while preventing any load from being transferred to the RF coil array 138. As the cradle 90 moves thru the magnet bore, and a scan is performed with use of the MR and PET systems, the CMA structure—and specifically the structural members 148 thereof—thus support the cradle with patient load and ensures a stable and small gap always exists between the patient cradle 90 and the RF coil array 138, such that no portion of the RF elements 136 mounted on the cover portion 130 are loaded or deformed during loading with patient weight, which would have potential to degrade image quality. The cover portion 130 of CMA structure 126 also has specifically designed openings that interface with the structural supports 148 of the CMA structure that help to move any fluids thru the roller support region without allowing fluids to enter the electronics 146 within the CMA structure 126.

As shown in FIGS. 3-7, according to an exemplary embodiment of the invention, each of base portion 128 and cover portion 130 of CMA structure 126 include a handle feature 156 formed integrally therewith that enables an operator to selectively remove the RF coil assembly structure 126 from patient support assembly 80 as desired. By providing for selective removal of the RF coil assembly structure 126 from patient support assembly 80 by way of handle 156, the number and arrangement of RF coil elements 136 in the RF coil assembly structure 126 can be changed by an operator to meet the requirements of a particular imaging scan being performed on a patient. It is recognized, however, that the CMA structure 126 does not have to be removable and could be permanently placed in the bridge 94, with the structure 126 only being removed only during maintenance or very special applications. Alternatively, it is recognized that the CMA structure 126 could be removable for use with other applications, such as Multi-Nuclear Spectroscopy (MNS), and that the CMA structure could be removed and a filler CMA be positioned in its place—with the filler having the same configuration but without RF coil elements.

Figure 8:
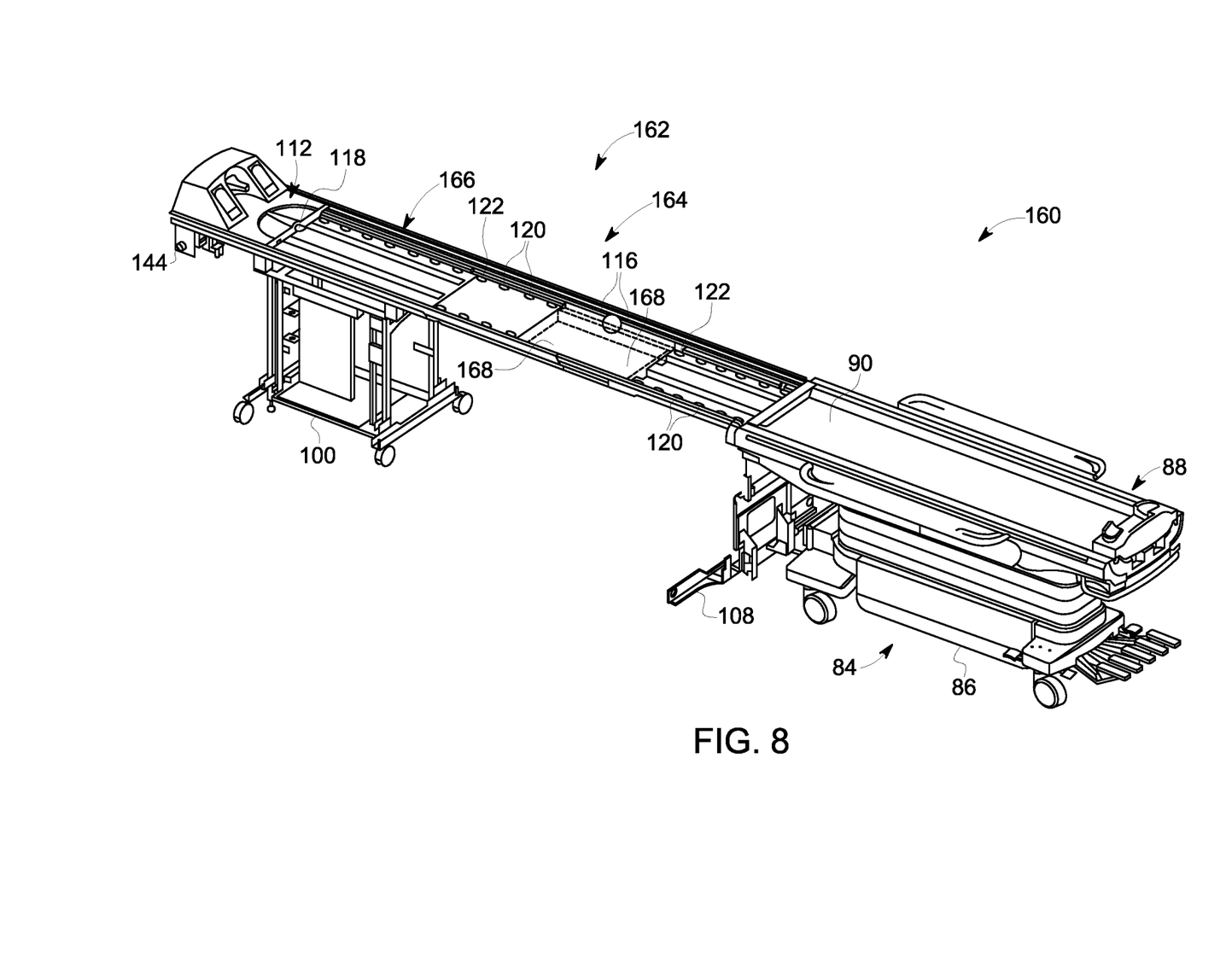
FIG. 8 is a perspective view of a patient support assembly for use in the PET-MR imaging system of FIG. 1 according to another embodiment of the invention.

Referring now to FIG. 8, a patient support assembly 160 is shown according to another embodiment of the invention. The patient support assembly 160 is substantially similar to the patient support assembly 80 shown in FIG. 2, and thus like elements are numbered as such in FIG. 8. Of primary difference is that a bridge assembly 162 of patient support assembly 160 includes a front bridge 164 and a rear bridge 166—where the front bridge is formed as a single unitary bridge structure rather than a "split bridge" structure as included in front bridge 92 of patient support assembly 80 in FIG. 2. The bridge assembly 162 provides a path for the patient cradle 90 to move within and through the bore 82 of imaging system 10 (FIG. 1) to move the patient to desired imaging locations within the imaging system.

Figure 9:
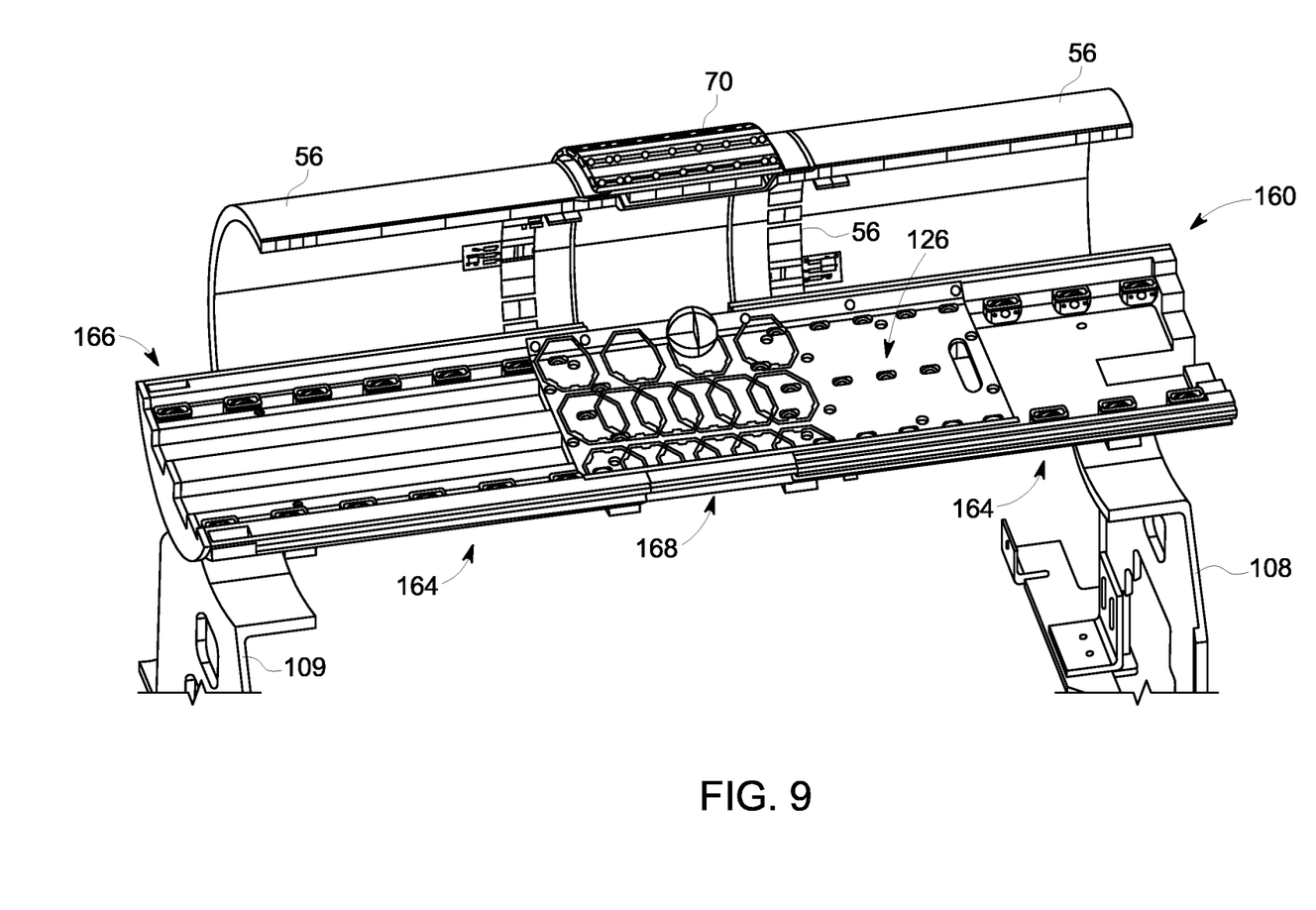
FIG. 9 is a view of a stationary posterior RF coil structure positioned relative to the patient support assembly of FIG. 6 according to an embodiment of the invention.

As shown in FIG. 8, and with reference also to FIG. 9, the front bridge 164 includes a cut-out area or portion 168 therein in an area coinciding with the position of PET detector array 70. The cut-out area 168 of front bridge 164 forms an area for housing the CMA structure 126 and the RF coil array 138 included therein. Detailed views of the CMA structure 126 are shown and described in detail in FIGS. 4-7, as set forth above, with the CMA structure 126 providing support for the cradle 90 with a patient load thereon as it traverse over the RF coil array 138 and ensuring a stable and small gap always exists between the patient cradle 90 and the RF coil array 138.

Beneficially, embodiments of the invention thus provide a stationary posterior RF coil structure 126 (i.e., CMA structure) for use in a stand-alone MR imaging system and/or a hybrid PET-MR system. The RF coil structure 126 is constructed so as to arrange RF coil elements 136 thereon that enables placement of the RF coil elements in good proximity with a patient anatomy and so as to provide a constant and uniform gap between the entire set of RF elements and a surface of a patient cradle 90, so as to enable good MR image quality. The RF coil structure 126 is further constructed to include structural elements 148 that enable the cradle 90 to roll over the posterior stationary RF coil array 138, as the cradle moves thru the magnet bore.

The stationary posterior RF coil structure 126 is constructed to have a minimal mass in the PET detector region (i.e., PET gap) by providing minimal electrical and mechanical components in the PET gap and moving all large mass components away from the PET gap, such that any unnecessary attenuation of gamma rays by the RF coil structure 126 that might reduce the PET signal to the detector array 70 is minimized, and any degradation of image quality is prevented.

Therefore, according to one embodiment of the invention, a PET-MRI apparatus includes a magnetic resonance imaging (MRI) system having a plurality of gradient coils positioned about a bore of a magnet, and an RF coil assembly coupled to a pulse generator to emit an RF pulse sequence and arranged to receive resulting MR signals from a subject of interest in the bore within an MR field-of-view (FOV). The PET-MRI apparatus also includes a positron emission tomography (PET) system having a detector array encircling the bore, with the detector array being controlled to acquire PET emissions of the subject of interest within a PET detector FOV, and a patient support assembly configured to provide for support and movement of the subject of interest through the bore to enable acquisition of the MR signals and the PET emissions from the subject of interest, the patient support assembly comprising a cradle configured to accommodate the subject of interest and a bridge configured to receive the cradle and provide for translation therealong. The PET-MRI apparatus further includes a stationary radio frequency (RF) coil structure positioned on the bridge so as to be between the bridge and the cradle and such that a portion of the RF coil structure is within the PET FOV, the RF coil structure comprising a base portion, a cover portion positioned over the base portion, an array of RF coil elements positioned on the cover portion so as to be positioned within the MR FOV and PET FOV, and driver electronics configured to control operation of the array of RF coil elements, the driver electronics being positioned within the base portion so as to be positioned outside of the PET FOV.

According to another embodiment of the invention, a stationary posterior RF coil structure for use in a stand-alone MR imaging system or a combination PET-MR imaging system includes a base portion, a cover portion positioned over the base portion, an array of RF coil elements positioned on the cover portion and, in a first region of the RF coil structure, and driver electronics configured to control operation of the array of RF coil elements, the driver electronics being positioned in the base portion, in a second region of the RF coil structure, so as to be separated from the array of RF coil elements. The cover portion further includes a bottom surface and a pair of contoured side surfaces extending up from the bottom surface, wherein the array of RF coil elements is arranged and positioned on the cover portion so as to extend from the bottom surface up the pair of contoured side surfaces.

According to yet another embodiment of the invention, an MR imaging apparatus includes an MRI system configured to acquire MR signals from a subject of interest, the MRI system having a plurality of gradient coils positioned about a bore of a magnet and an RF coil assembly coupled to a pulse generator to emit an RF pulse sequence. The MR imaging apparatus also includes a patient support assembly configured to provide for support and movement of the subject of interest through the bore to enable acquisition of the MR signals from the subject of interest, the patient support assembly comprising a cradle configured to accommodate the subject of interest and a bridge configured to receive the cradle and provide for translation therealong. The MR imaging apparatus further includes a central matrix array (CMA) structure positioned on the bridge so as to be between the bridge and the cradle, the CMA structure comprising a base portion, a cover portion attached to the base portion so as to be positioned between the base portion and the cradle, an array of RF coil elements positioned on the cover portion, and a plurality of structural members extending upward from a bottom surface of the base portion, the plurality of structural members being configured to fully support a load applied by the cradle as the cradle translates the subject of interest through the bore, without any of the load being transferred to the array of RF coil elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A PET-MRI apparatus comprising:
   a magnetic resonance imaging (MRI) system having a plurality of gradient coils positioned about a bore of a magnet, and an RF coil assembly coupled to a pulse generator to emit an RF pulse sequence and arranged to receive resulting MR signals from a subject of interest in the bore within an MR field-of-view (FOV);
   a positron emission tomography (PET) system having a detector array encircling the bore, with the detector array being controlled to acquire PET emissions of the subject of interest within a PET detector FOV;
a patient support assembly configured to provide for support and movement of the subject of interest through the bore to enable acquisition of the MR signals and the PET emissions from the subject of interest, the patient support assembly comprising a cradle configured to accommodate the subject of interest and a bridge configured to receive the cradle and provide for translation therealong; and
a stationary radio frequency (RF) coil structure positioned on the bridge so as to be between the bridge and the cradle and such that a portion of the RF coil structure is within the PET FOV, the RF coil structure comprising:
a base portion;
a cover portion positioned over the base portion;
an array of RF coil elements positioned on the cover portion so as to be positioned within the MR FOV and PET FOV; and
driver electronics configured to control operation of the array of RF coil elements, the driver electronics being positioned within the base portion so as to be positioned outside of the PET FOV;
wherein the cover portion is contoured so as to match a shape of the cradle; and
wherein the array of RF coil elements is arranged and positioned on the cover portion so as to follow the contours of the cover portion, such that a constant and uniform gap is provided between the array of RF coil elements and the cradle.

2. The PET-MRI apparatus of claim 1, wherein the cover portion comprises a pair of wings formed on opposing sides of a center area, with the pair of wings of the cover portion being contoured such that the RF coil elements positioned thereon are angled so as to point toward a body of the subject-of-interest.

3. The PET-MRI apparatus of claim 1, wherein the base portion comprises:
a plurality of mounting columns extending upward from a bottom surface of the base portion;
a roller element positioned on a top surface of each of the plurality of mounting columns, the roller elements being positioned and arranged to engage a bottom surface of cradle;
wherein the plurality of mounting columns and the respective roller elements are configured to fully support a load applied by the cradle as the cradle translates the subject-of-interest through the bore, without any of the load being transferred to the array of RF coil elements.

4. The PET-MRI apparatus of claim 3, wherein at least a majority of the plurality of mounting columns are formed on the bottom surface of the base portion at locations outside of the PET FOV.

5. The PET-MRI apparatus of claim 3, wherein the cover portion of the RF coil structure includes a plurality of openings therein at locations corresponding to the roller elements, such that the roller elements protrude up through the plurality of openings to engage the bottom surface of the cradle.

6. The PET-MRI apparatus of claim 1, wherein the base portion comprises a handle formed integrally therewith to provide for selective removal of the RF coil structure from the bridge.

7. The PET-MRI apparatus of claim 1, wherein the bridge comprises:
a rear bridge; and
a front bridge connected to the rear bridge, the front bridge including:
a first section extending from a first edge of the PET tube into the volume of the bore; and
a second section extending from a second edge of the PET tube into the volume of the bore, wherein the second section is spaced apart from the first section so as to form a gap in the front bridge between the first section and the second section in an area adjacent the detector array of the PET system.

8. The PET-MRI apparatus of claim 7, wherein the front bridge includes a coil positioning area formed therein configured to house the RF coil structure therein, the coil positioning area including portions of the first and second sections of the front bridge adjacent one another and including the gap formed between the first section and the second section.

9. A stationary posterior radio frequency (RF) coil structure for use in a stand-alone magnetic resonance (MR) imaging system or a combination positron emission tomography (PET)-MR imaging system, the RF coil structure comprising:
a base portion;
a cover portion positioned over the base portion;
an array of RF coil elements positioned on the cover portion and, in a first region of the RF coil structure;
driver electronics configured to control operation of the array of RF coil elements, the driver electronics being positioned in the base portion, in a second region of the RF coil structure, so as to be separated from the array of RF coil elements; and
a plurality of structural members formed in the base portion, each of the plurality of structural members including a vertically oriented roller element positioned on a top surface thereof;
wherein the plurality of structural members are configured to fully support a load applied to the RF coil structure without any of the load being transferred to the array of RF coil elements, the load comprising a load applied by a cradle translating a patient through a bore of the stand-alone MR imaging system or combination PET-MR imaging system;
wherein the cover portion further comprises:
a bottom surface; and
a pair of contoured side surfaces extending up from the bottom surface;
wherein the array of RF coil elements is arranged and positioned on the cover portion so as to extend from the bottom surface up the pair of contoured side surfaces.

10. The RF coil structure of claim 9, wherein a majority of the plurality of structural members are located outside of the first region of the RF coil structure.

11. The RF coil structure of claim 9, wherein the arranging and positioning of the RF coil elements on the cover portion so as to extend from the bottom surface up the pair of contoured side surfaces provides a constant and uniform gap between the array of RF coil elements and the cradle.

12. The RF coil structure of claim 9, wherein the cover portion of the RF coil structure includes a plurality of openings therein at locations corresponding to the roller elements, such that the roller elements protrude up through the plurality of openings to engage the bottom surface of cradle.

13. The RF coil structure of claim 9, wherein each of the base portion and the cover portion comprises a handle formed integrally therewith to provide for selective removal of the RF coil structure from the stand-alone MR imaging system or combination PET-MR imaging system.

\* \* \* \* \*